United States Patent [19]
Brennan

[11] Patent Number: 5,472,672
[45] Date of Patent: Dec. 5, 1995

[54] APPARATUS AND METHOD FOR POLYMER SYNTHESIS USING ARRAYS

[75] Inventor: Thomas M. Brennan, San Francisco, Calif.

[73] Assignee: The Board of Trustees of the Leland Stanford Junior University, Stanford, Calif.

[21] Appl. No.: 142,593

[22] Filed: Oct. 22, 1993

[51] Int. Cl.[6] ................................................. B01J 19/00
[52] U.S. Cl. ........................ 422/131; 422/110; 422/111; 422/116
[58] Field of Search ................................ 422/110, 111, 422/131, 116

[56] References Cited

U.S. PATENT DOCUMENTS

| | | |
|---|---|---|
| 4,458,066 | 7/1984 | Caruthers et al. . |
| 4,500,707 | 2/1985 | Caruthers et al. . |
| 5,047,524 | 9/1991 | Andrus et al. . |
| 5,106,583 | 4/1992 | Raysberg et al. . |

OTHER PUBLICATIONS

Gerpen, *J. Org. Chem.* 56, 6659–6666, (1991) Bray et al.
Fodor, et al., *Science* 251, 767 (1991).
Khrapko, et al., *FEBS Letters* 256, 118 (1989).
Oligonucleotides and Analogues: A Practical Approach, F. Exkstein, Ed. IRL Press, Oxford University; Oligonucleotide Synthesis: A Practical Approach, Gait, Ed., IRL Press, Washington, D.C.

Primary Examiner—Timothy M. McMahon
Attorney, Agent, or Firm—Flehr, Hohbach, Test, Albritton & Herbert

[57] ABSTRACT

A polymer synthesis apparatus (20) for building a polymer chain including a head assembly (21) having an array of nozzles (22) with each nozzle coupled to a reservoir (23) of liquid reagent (24), and a base assembly (25) having an array of reaction wells (26). A transport mechanism (27) aligns the reaction wells (26) and selected nozzles (22) for deposition of the liquid reagent (24) into selected reaction wells (26). A sliding seal (30) is positioned between the head assembly (21) and the base assembly (25) to form a common chamber (31) enclosing both the reaction well (26) and the nozzles (22) therein. A gas inlet (70) into the common chamber (31), upstream from the nozzles (22), and a gas outlet (71) out of the common chamber (31), downstream from the nozzles (22), sweeps the common chamber (31) of toxic fumes emitted by the reagents. Each reaction well (26) includes an orifice (74) extending into the well (26) which is of a size and dimension to form a capillary liquid seal to retain the reagent solution (76) in the well (26) for polymer chain growth therein. A pressure regulating device (82) is provided for controlling a pressure differential, between a first gas pressure exerted on the reaction well (26) and a second gas pressure exerted on an exit (80) of the orifice, such that upon the pressure differential exceeding a predetermined amount, the reagent solution (76) is expelled from the well (26) through the orifice (74). A method of synthesis of a polymer chain in a synthesis apparatus (20) is also included.

28 Claims, 9 Drawing Sheets

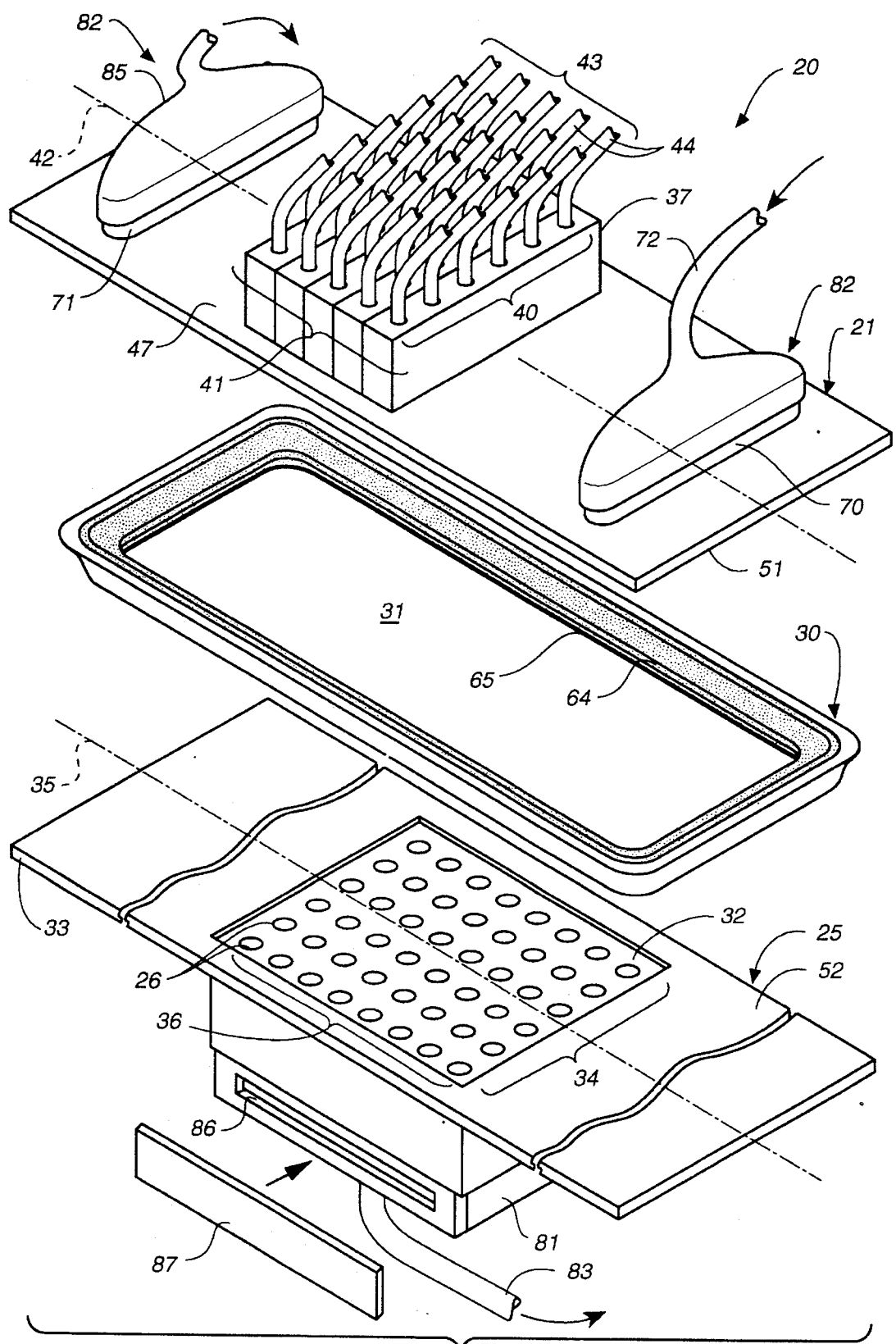
FIG._1

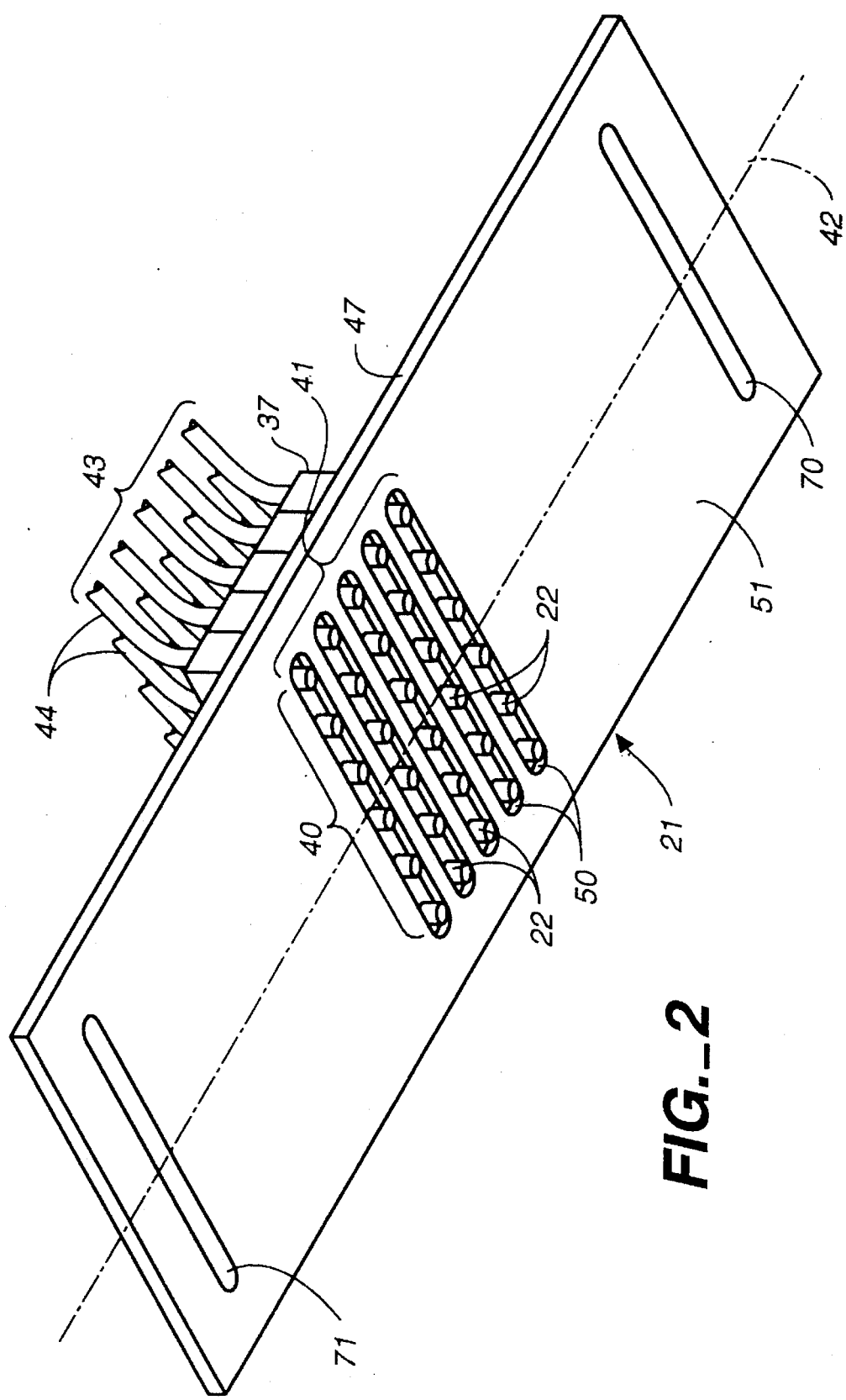
FIG._2

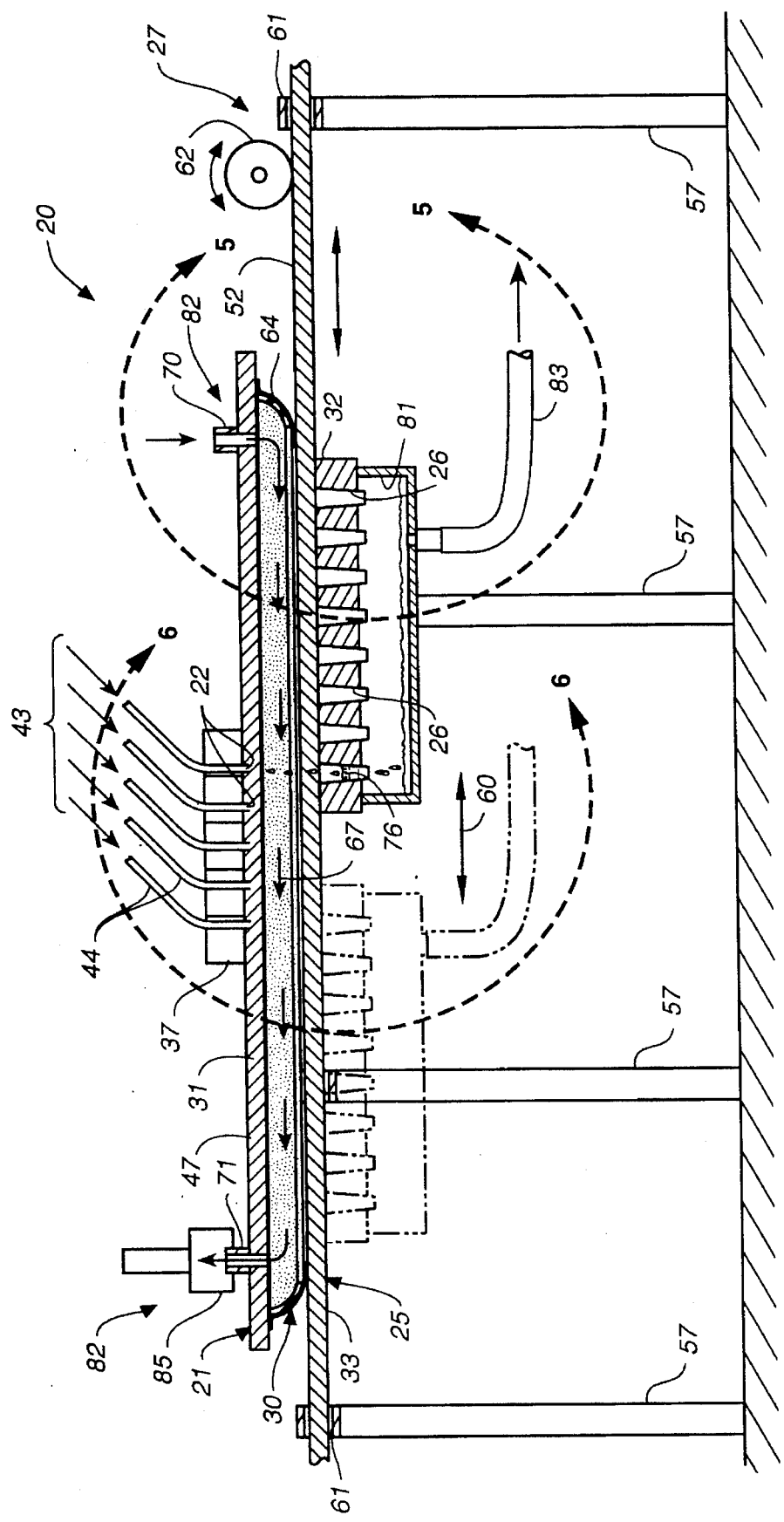
FIG._3

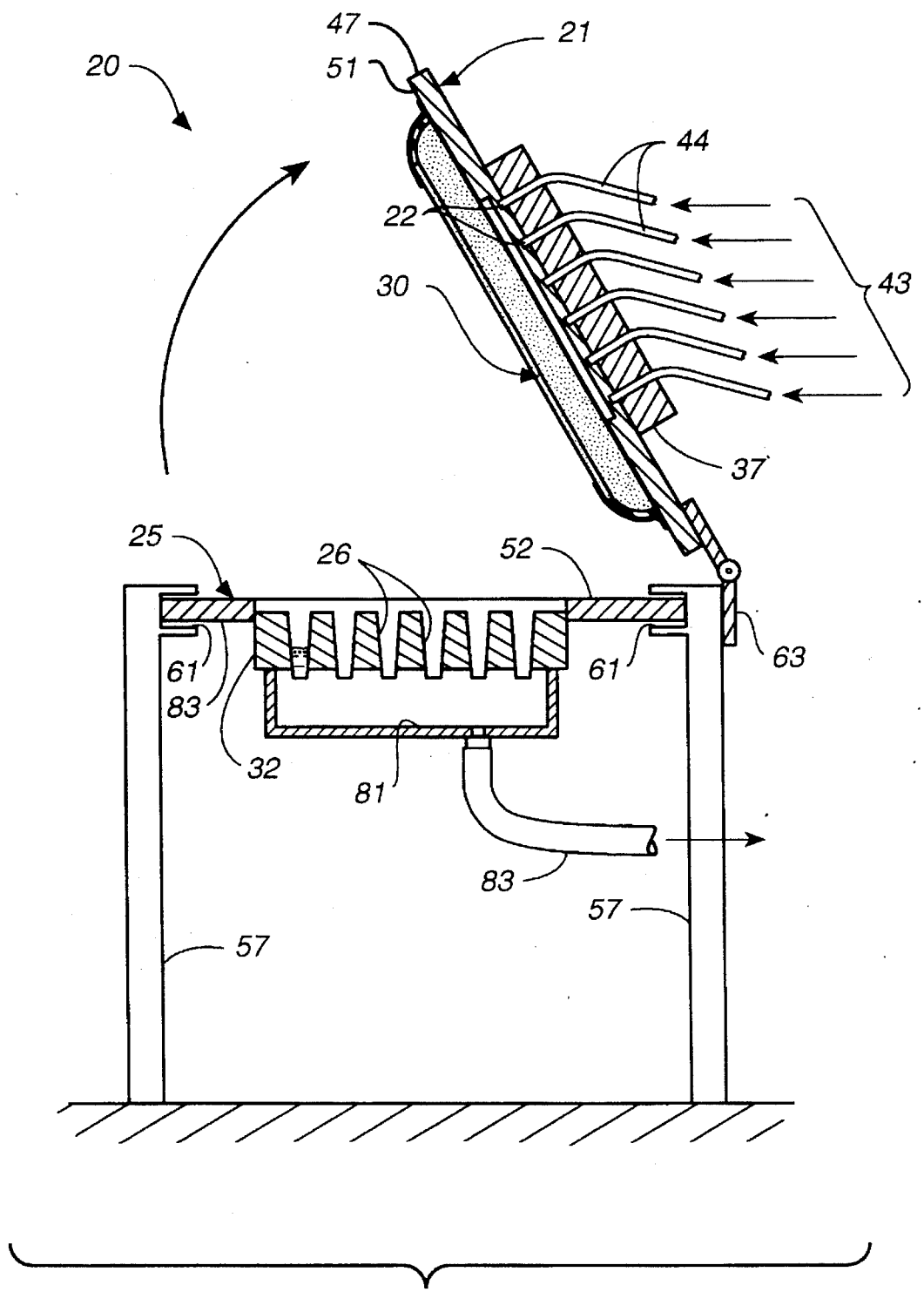
FIG._4

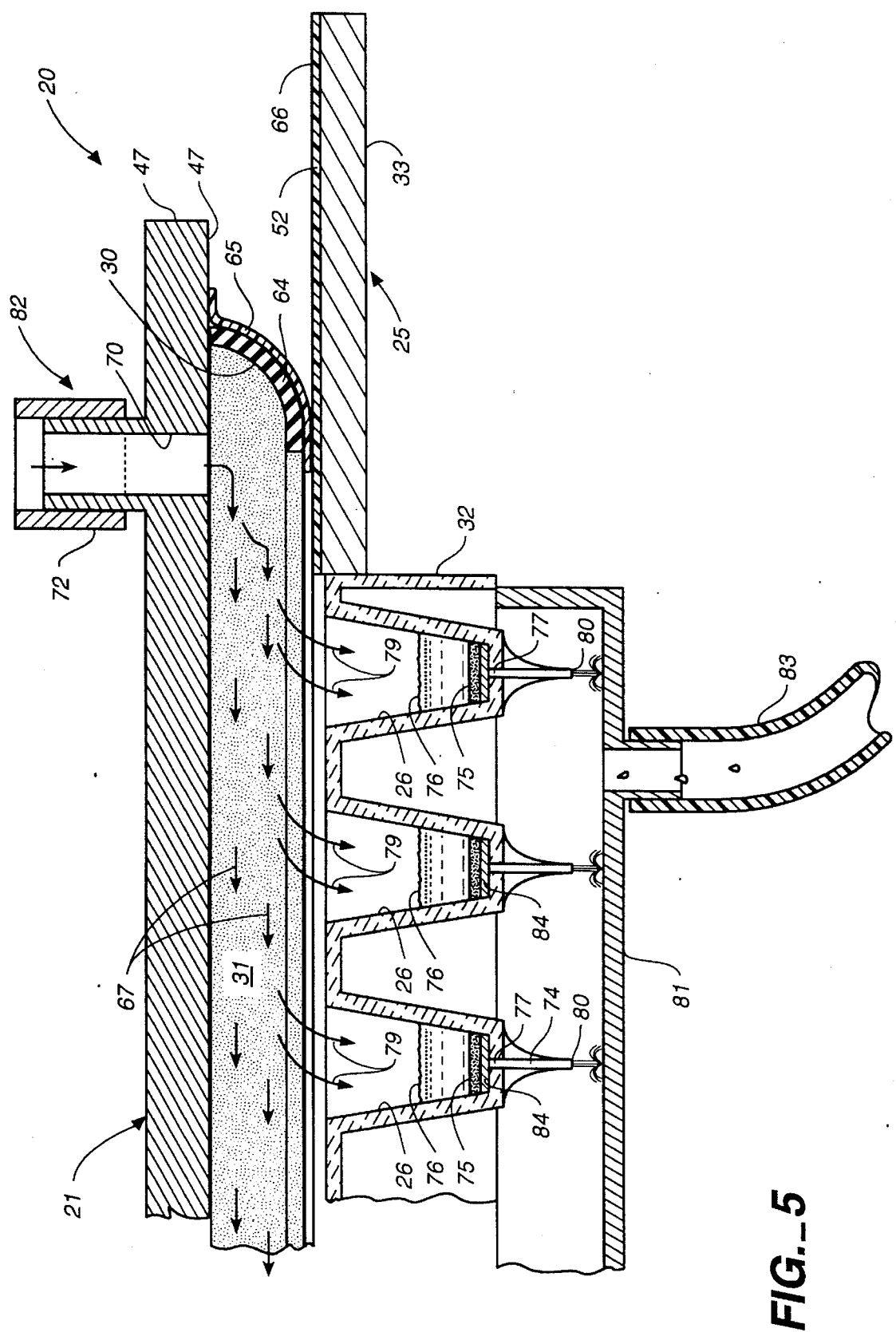
FIG._5

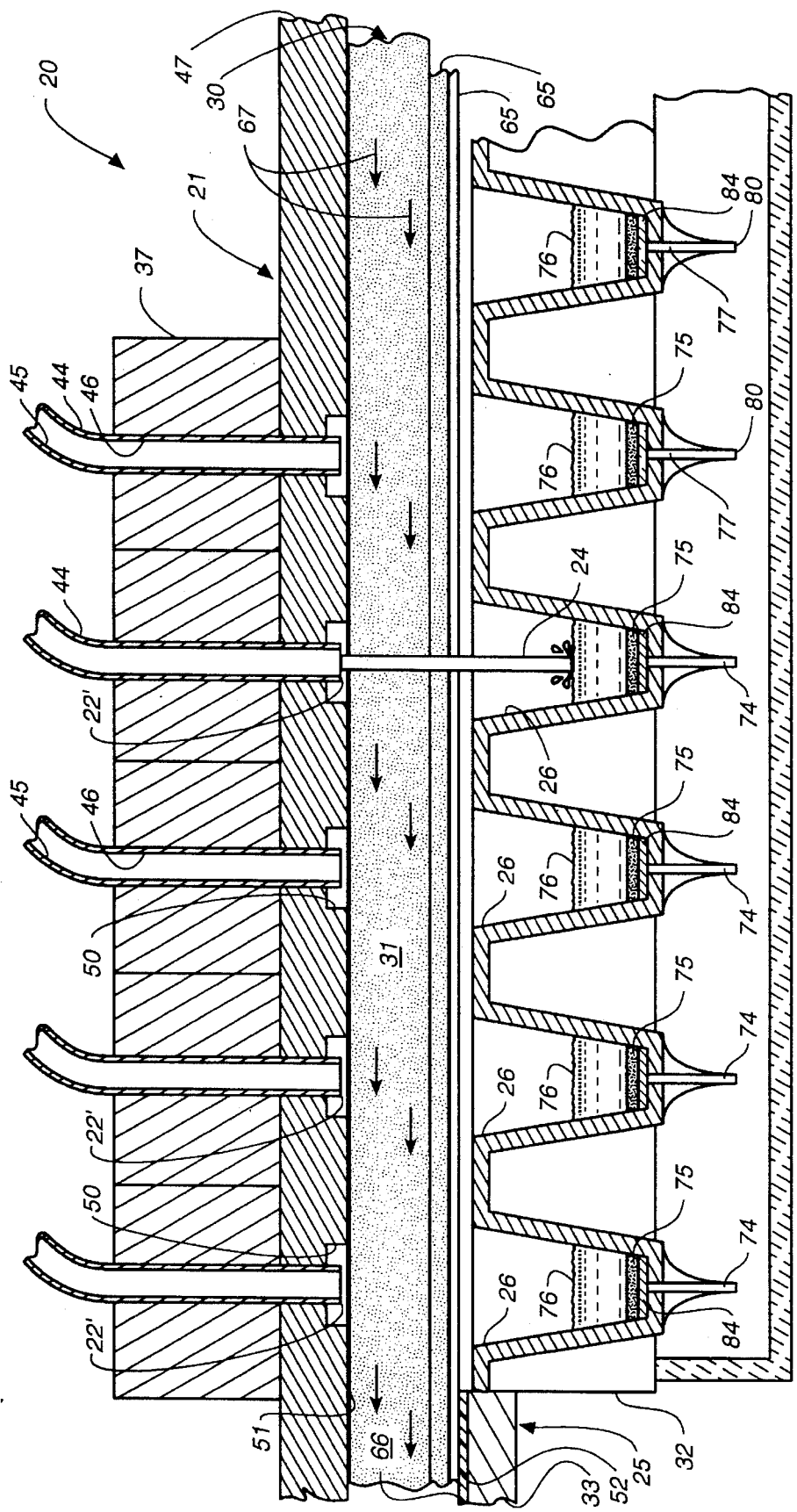
FIG._6

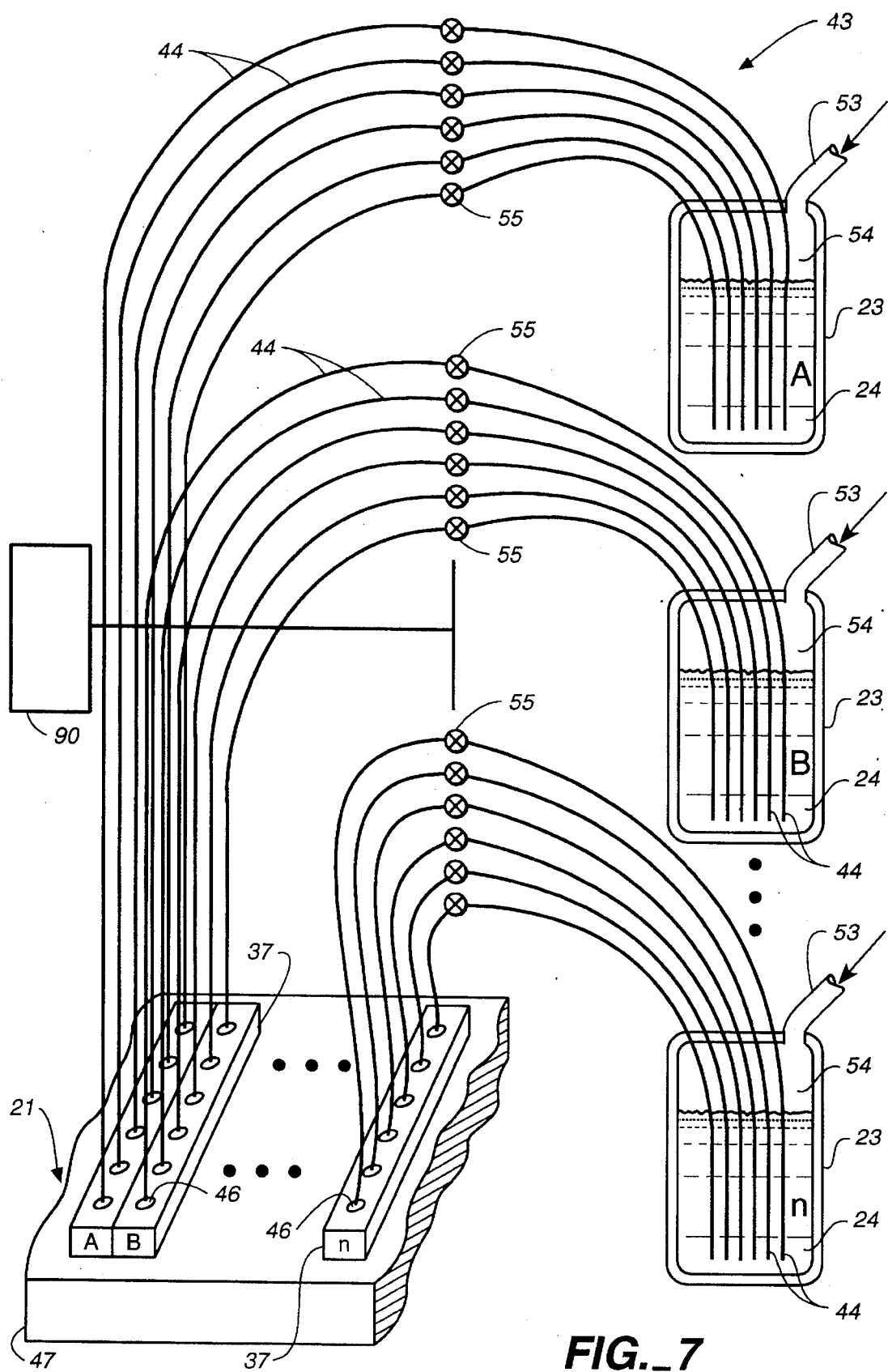
FIG._7

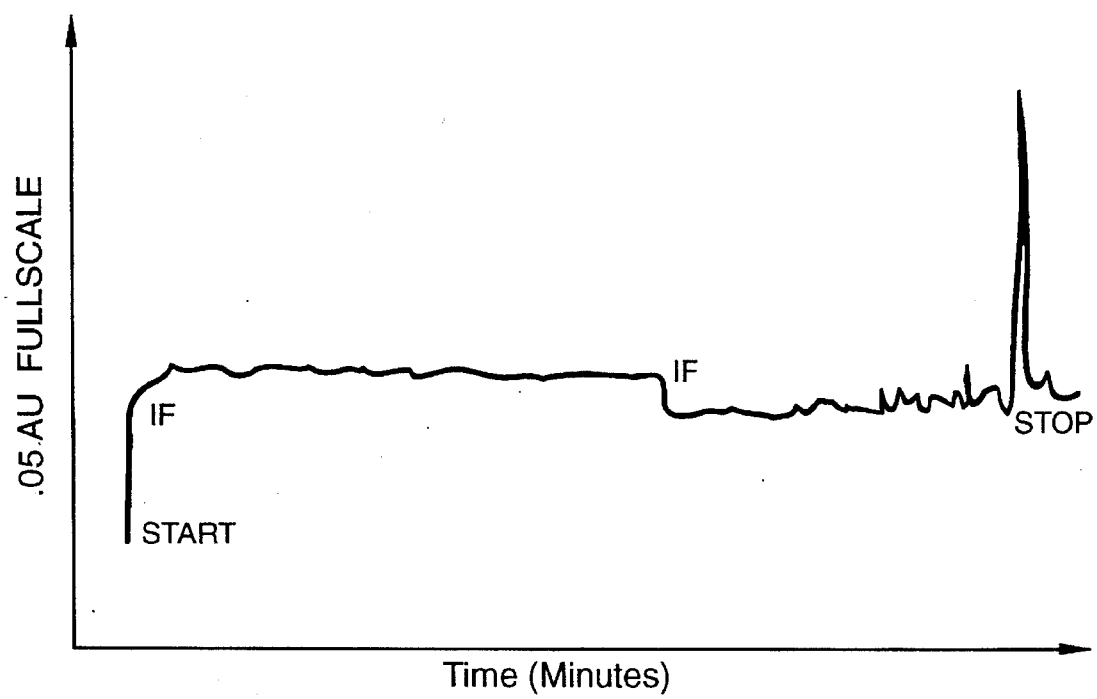
RUN #116
WORKFILE ID: C
WORKFILE NAME:
TOTAL AREA = 757390
MUL FACTOR = 1.0000E + 00
AREA %
| RT | AREA | TYPE | AR / HT | AREA % |
|---|---|---|---|---|
| 8.56 | 15630 | VB | 0.054 | 2.064 |
| 9.81 | 10112 | BB | 0.037 | 1.335 |
| 10.36 | 10365 | PB | 0.050 | 1.369 |
| 10.48 | 16847 | BB | 0.057 | 2.224 |
| 10.61 | 31631 | BB | 0.084 | 4.176 |
| 10.78 | 11126 | PB | 0.034 | 1.469 |
| 11.01 | 10483 | PB | 0.047 | 1.384 |
| 11.26 | 26949 | BB | 0.045 | 3.558 |
| 11.64 | 31930 | BB | 0.058 | 4.216 |
| 11.82 | 16944 | VB | 0.047 | 2.237 |
| 12.06 | 20256 | VB | 0.075 | 3.731 |
| 12.42 | 26993 | PB | 0.052 | 6.564 |
| 12.64 | 40742 | BB | 0.045 | 5.379 |
| 12.79 | 10509 | VB | 0.034 | 1.388 |
| 13.04 | 13205 | BB | 0.029 | 1.744 |
| 13.31 | 17940 | PB | 0.033 | 2.369 |
| 13.38 | 412520 | BB | 0.089 | 54.467 |
| 13.77 | 25202 | PB | 0.069 | 3.328 |
*FIG._8A*

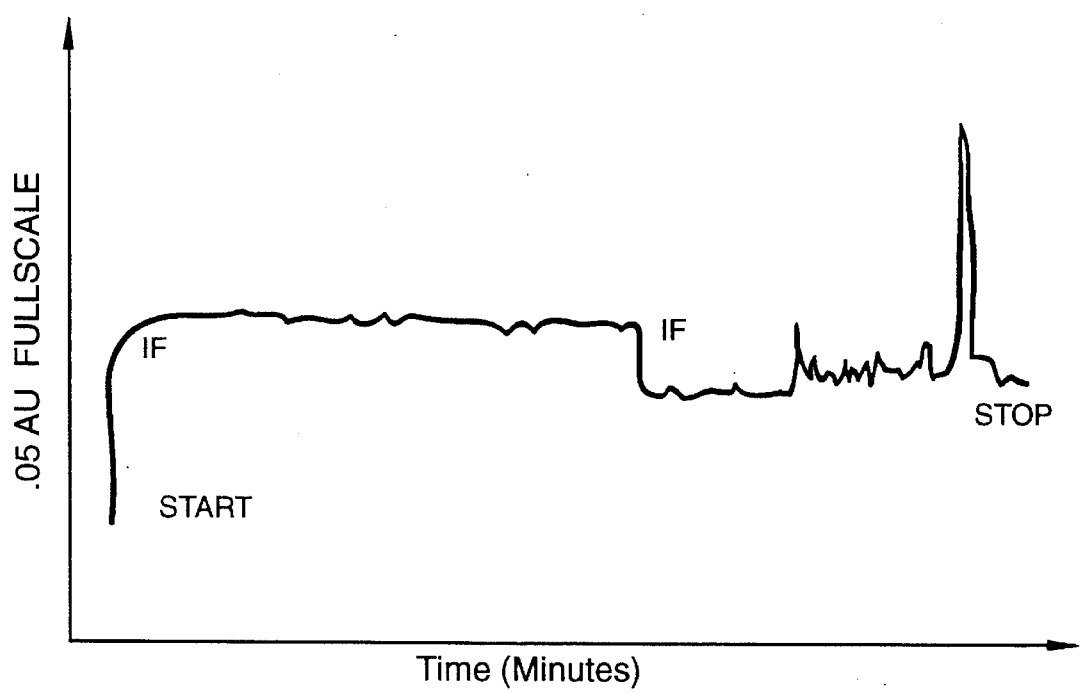
```
RUN #115
WORKFILE ID: C                TOTAL AREA = 563000
WORKFILE NAME:                MUL FACTOR = 1.0000E + 00
AREA %
   RT      AREA     TYPE    AR / HT     AREA %
  10.40    54453     BB      0.057       9.657
  10.47    23838     BB      0.048       4.228
  10.66    35480     BB      0.072       6.292
  10.93    11016     BB      0.039       1.954
  11.16    41408     VB      0.073       7.343
  11.54    14864     PB      0.059       2.636
  11.79    14056     BB      0.037       2.493
  11.95    16643     PB      0.041       2.952
  12.12    11510     PB      0.040       2.041
  12.21    23744     BB      0.045       4.211
  12.34    27969     BB      0.055       4.960
  12.79   272420     VB      0.071      48.311
  13.01    16486     BB      0.063       2.924
```
FIG._8B

APPARATUS AND METHOD FOR POLYMER SYNTHESIS USING ARRAYS

This invention was made with Government support under contract DOE LBL 4437-10 awarded by the Department of Energy and contract 3POI HG00205-0251 awarded by the National Institutes of Health. The Government has a certain rights in this invention.

TECHNICAL FIELD

The present invention relates, generally, to polymer synthesis apparatus, and, more particularly, relates to polymer synthesis apparatus using arrays.

BACKGROUND ART

In the recent past, oligonucleotides have played an increasing and more pivotal role in diagnostic medicine, forensic medicine and molecular biology research. One primary function of these polymers, in particular, is their use in gene probe assays for the detection of specific nucleic acid sequences.

Gene probe assays are used for a variety of purposes, including: genetic counseling; tissue typing; and molecular biology research. For example, an individual may be tested to see if he or she carries the gene for Huntington's disease or cystic fibrosis. Another use of gene probe assays include determining compatibility prior to tissue transplantation, and for matching up tissue or blood samples for forensic medicine. Finally, in molecular biology research, these assays are extensively employed to explore homologies among genes from different species, and to clone genes for which only a partial nucleic acid or amino acid sequence is known, such as in the polymerase chain reaction (pcr).

These types of assays typically test for the presence of a specific nucleic acid sequence, usually a DNA sequence, although RNA sequences may be employed as well. As is well known in the field, this is accomplished utilizing oligonucleotides synthesized to have specific, predetermined sequences. The sequence of an oligonucleotide probe may be based on known amino acid sequences, known DNA sequences, or may be a "guess" probe, based on homology to known or putative DNA or amino acid sequences. Since DNA is a "degenerate" code, and several DNA sequences will result in a single amino acid sequence, gene probe assays based on an amino acid sequence frequently utilize pools of related oligonucleotides; each having a different specific sequence of nucleotides. Thus it is often necessary to create a large number of related but distinct oligonucleotides to clone a single gene.

In addition to the actual sequence, there are a number of parameters which may be altered in the synthesis of oligonucleotides. It is also frequently necessary to synthesize these polymers in a variety of lengths, since generally, the longer the oligonucleotide probe, the more specific the gene probe assay will be; specificity may or may not be desired in any particular application. Oligonucleotides may be made of deoxyribonucleotides, or ribonucleotides, or mixtures. Alternatively, oligonucleotides with modified or non-standard bases or non-radioactive labels incorporated may be desirable. Similarly, oligonucleotides with altered ribose-phosphate backbones may be created for some applications.

There are several other uses of oligonucleotides besides the gene probe assay use. For example, the formation of a single stranded oligonucleotide with a specific sequence may be used in the formation of extremely stable triplex DNA structures. Other uses include direct construction of synthetic genes and plasmid vectotrts by ligating or joining together the component 5'-phosphate oligonucleotides.

Accordingly, as the use of synthetic oligonucleotides has increased, so has its demand. In turn, this has spawned development of new synthesis apparatus and methodologies for basic procedures for custom sequence defined oligonucleotides. These apparatus and methods, however, are generally very expensive to employ and not readily available for mass production thereof. Typically, the present generation automated DNA sequential synthesizers place a derivatized solid support, such as controlled pore glass (CPG), into an individual reaction chamber of a column to provide a stable anchor on which to initiate solid phase synthesis. Using a series of complex valving, and pumps coupled to the column, the appropriate selected reagents are sequentially filtrated through the chamber in a predetermined manner. Contact of the reagent with the polymer units pre-affixed to the CPG, which is retained and supported in the chamber by a sample support porous frit, causes a reaction resulting in sequenced growth thereon.

While each column of this assembly is effective to rapidly mass produce a homogenous population of sequence defined oligonucleotides, the current assemblies only offer four (4) column capabilities. Increased column capacity is limited due to physical limitations of the valving configuration. Hence, only four independent synthesis cycles can be performed simultaneously. Further, since the synthesis apparatus is not generally amenable to integrated automation with other robotic lab instrumentation, an operator must intervene to load and remove each individual synthesis column manually. Such handling increases human error.

A more important limitation is that all the reagents are funneled through a common manifold passage. Only one reagent or combination thereof, thus, can be simultaneously deposited in selected columns. For example, the reagent "tetrazole" cannot be deposited in column one while a particular amidite reagent is simultaneously being deposited in column four. In addition, for each independent synthesis or reaction, the common manifold passage and associated valving must be flushed with a cleansing reagent so that residual amidite or deblocking reagents will not be undesirably deposited in a column. This approach wastes time, as well as increasing operator costs.

Synthesis of arrays of bound oligonucleotides or peptides is also generally known in the art. In one approach to parallel synthesis, known as the Tea-bag?? method or disk design, an array of individual packets or disks of solid support beads are physically sorted into four (4) amidite subsets for treatment with the selected amidite. After each packet of beads has been treated with the common reagent, the packets must again be manually resorted into the four subsets for the subsequent synthesis cycle. Such sorting and resorting becomes too burdensome and labor intensive for the preparation of large arrays of oligonucleotides.

Another approach using arrays is the pin dipping method for parallel oligonucleotide synthesis. Geysen, *J. Org. Chem.* 56, 6659 (1991). In this method, small amounts of solid support are fused to arrays of solenoid controlled polypropylene pins, which are subsequently dipped into trays of the appropriate reagents. The density of arrays, however, is limited, and the dipping procedure employed is cumbersome in practice.

Disclosed at the Southern, Genome Mapping Sequence Conference, May 1991, Cold Spring Harbour, N.Y., is still another scheme for oligonucleotide array synthesis in which selected areas on a glass plate are physically masked and the desired chemical reaction is carried out on the unmasked portion of the plate. The problem with this method is that it is necessary to remove the old mask and apply a new one after each interaction. Fodor et al., *Science* 251, 767 (1991) describes another method for synthesizing very dense 50 micron arrays of peptides (and potentially oligonucleotides) using mask-directed photochemical deprotection and synthetic intermediates. This method is limited by the slow rate of photochemical deprotection and by the susceptibility to side reactions (e.g., thymidine dimer formation) in oligonucleotide synthesis. Khrapko et al., *FEBS Letters* 256, 118 (1989) suggest simplified synthesis and immobilization of multiple oligonucleotides by direct synthesis on a two-dimensional support, using a printer-like device capable of sampling each of the four nucleotides into given dots on the matrix. However, no particulars about how to make or use such a device are provided.

In summary, the related art generally contains numerous ideas and information related to the synthesis of arrays of oligonucleotides or peptides for the determination of nucleotide sequences or the amino acid sequences of specific binding peptides. However, existing or suggested methods are limited, and do not conveniently and reliably mass produce very large arrays necessary for effective large-scale sequencing.

DISCLOSURE OF INVENTION

Accordingly, it is an object of the present invention to provide a polymer synthesis apparatus and method for building sequence defined polymer chains.

Another object of the present invention is to provide a polymer synthesis apparatus and method for preparing large quantity arrays of oligonucleotides or peptides in a reproducible and rapid manner.

Yet another object of the present invention is to provide a polymer synthesis apparatus and method which reduces reagent waste during the preparation of large quantity arrays of oligonucleotides.

Still another object of the present invention is to provide a polymer synthesis apparatus and method for preparing large quantity arrays of oligonucleotide at reduced costs.

It is a further object of the present invention to provide a polymer array synthesis apparatus and method which is durable, compact, easy to maintain, has a minimum number of components, is easy to use by unskilled personnel, and is economical to manufacture.

In accordance with the foregoing objects, one embodiment of the present invention provides a polymer synthesis apparatus for building a polymer chain by sequentially adding polymer units in a reagent solution. The synthesis apparatus comprises a head assembly having a plurality of nozzles mounted thereto in generally spaced-apart relation. Each nozzle is coupled to a reservoir of liquid reagent for controlled delivery therethrough. Further, a base assembly is included having at least one reaction well, and a transport mechanism coupled to at least one of the head assembly and the base assembly to produce relative movement therebetween. This positions the reaction well and a selected one nozzle in alignment for deposition of a liquid reagent into the reaction well for synthesis of a polymer chain. A sliding seal is positioned between the head assembly and the base assembly to form a common chamber enclosing both the reaction well and the nozzles therein.

The synthesis apparatus may further include an inlet into the common chamber positioned upstream from the nozzles, and an outlet out of the common chamber positioned downstream from the nozzles. A pressurized gas source is coupled to the inlet for continuously streaming a gas through the common chamber from the chamber upstream to the chamber downstream and out of the outlet to sweep the common chamber of toxic fumes emitted by the reagents, as well as keep air and moisture from seeping in.

In another aspect of the present invention, a polymer synthesis apparatus is provided comprising a base assembly including a reaction well, and having at least one orifice extending into the well. At least one solid support is disposed in the well for growing and immobilizing a polymer chain thereon. Reagent solution in the well is in contact with the solid support and at least one polymer unit of the polymer chain affixed to the solid support. Further, a retaining device is included positioned in the well, and is formed and dimensioned to substantially prevent passage of the solid support through the orifice. The orifice has an entrance into the well and an exit out of the well, and is of a size and dimension to form a capillary liquid seal to retain the reagent solution in the well to enable polymer chain growth therein. To retain the solution in the well, a pressure differential between a first gas pressure exerted on the reaction well and a second gas pressure exerted on the orifice exit must be less than a predetermined amount. Finally, a pressure regulating device is provided for controlling the pressure differential such that upon the pressure differential exceeding the predetermined amount, the reagent solution is expelled from the well through the orifice.

The present invention also includes a method of synthesis of a polymer chain in a synthesis apparatus comprising the steps of: A) aligning the reaction well and a selected one nozzle through the transport mechanism coupled to at least one of the head assembly and the base assembly to produce relative movement therebetween; and B) depositing a liquid reagent into the well from the reagent reservoir through the one nozzle to enable synthesis of a polymer chain. Finally, C) sweeping toxic fumes, emitted by the reagents, from the common chamber through passage of a gas from a pressurized gas source, coupled to an inlet into the common chamber and positioned upstream from the nozzles, and out of the chamber through an outlet out from the common chamber and positioned downstream from the nozzles.

Another method of polymer synthesis is provided for building a polymer chain by sequentially adding polymer units to at least one solid support for growing and immobilizing a polymer chain thereon in a liquid reagent. The method comprises the steps of A) depositing a liquid reagent in the reaction well, having a properly sized orifice, in contact with at least one solid support and at least one polymer unit of the polymer chain affixed to the solid support, and forming a capillary liquid seal to retain the reagent solution in the well to enable polymer chain growth on the solid support. The next step includes B) applying a first gas pressure to the reaction well such that a pressure differential between the first gas pressure and a second gas pressure exerted on an exit of the orifice exceeds a predetermined amount necessary to overcome the capillary liquid seal and expel the reagent solution from the well through the orifice.

BRIEF DESCRIPTION OF THE DRAWING

The assembly of the present invention has other objects and features of advantage which will be more readily apparent from the following description of the Best Mode of Carrying Out the Invention and the appended claims, when taken in conjunction with the accompanying drawing, in which:

FIG. 1 is an exploded top perspective view of the polymer synthesis array apparatus constructed in accordance with the present invention.

FIG. 2 is bottom perspective view of a head assembly of the polymer synthesis array apparatus of FIG. 1 illustrating the recessed nozzle ends.

FIG. 3 is a side elevation view, in cross-section of the polymer synthesis array apparatus of FIG. 1 and showing the sweeping action of the flow of inert gas through the common chamber.

FIG. 4 is a front elevation view, in cross-section of the polymer synthesis array apparatus of FIG. 1 and illustrating the head assembly pivotally mounted to a frame assembly.

FIG. 5 is an enlarged side elevation view, in cross-section, of the polymer synthesis array apparatus taken substantially along the line 5—5 of FIG. 3 and showing the capillary liquid seal formed between the liquid reagent solution and the corresponding frit and orifice.

FIG. 6 is an enlarged side elevation view, in cross-section, of the polymer synthesis array apparatus taken substantially along the line 6—6 of FIG. 3 and illustrating the balloon seal gasket.

FIG. 7 is an enlarged, schematic, top perspective view of a delivery assembly mounted to the head assembly of the polymer synthesis array apparatus.

FIGS. 8A and 8B depict the results of capillary electrophoresis runs of oligonucleotides Nos. 14 and 15, respectively, from Example 1.

BEST MODE OF CARRYING OUT THE INVENTION

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Attention is now directed to FIGS. 1 and 2 where a polymer synthesis apparatus, generally designated 20, is shown for building a polymer chain by sequentially adding polymer units to a solid support in a liquid reagent. Incidently, while apparatus 20 is particularly suitable for building sequence defined oligonucleotides, the present invention may be employed for synthesis of any polymer chain. Hence, the term "polymer unit" will be defined as a moiety that is bound to other moieties of the same or a different kind to form a polymer chain, such as olignucleotides and peptide chains.

In one embodiment, the synthesis apparatus 20, briefly, comprises a head assembly, generally designated 21, having a plurality of nozzles 22 (FIG. 2) mounted thereto in generally spaced-apart relation. Each nozzle 22 is coupled to a reservoir 23 (FIG. 7) of liquid reagent 24 for controlled delivery therethrough. Further, a base assembly, generally designated 25, is included having at least one reaction well 26, and a transport mechanism, generally designated 27 (FIG. 3), coupled to at least one of head assembly 21 and base assembly 25 to produce relative movement therebetween. This positions a selected reaction well 26 and a selected nozzle 22 in alignment for deposition of a selected liquid reagent 24 into the reaction well for synthesis of a polymer chain. A sliding seal, generally designated 30, is positioned between the head assembly and the base assembly to form a common chamber 31 (FIG. 3) which encloses both the reaction well and the nozzles therein.

In the preferred embodiment, an array of wells 26 (FIG. 1) is provided formed in a microtiter plate 32 which is carried by a sliding plate 33 of base assembly 25. The synthesis apparatus is particularly configured to employ a 96-well microtiter plate (not all wells shown for ease of illustration), aligned in 12 equally spaced-apart rows 34, each extending transverse to a longitudinal axis 35 of elongated base assembly 25, by 8 equally spaced-apart columns 36 wide. Microtiter plate 32 is preferably fabricated from a chemically inert material such as polypropylene. It of course will be appreciated that any number of wells, or arrangement of rows and columns, could be employed without departing from the true spirit and nature of the present invention.

FIGS. 1 and 2 further illustrate that nozzles 22, mounted to mounting blocks 37 of head assembly 21, are further aligned in an array of nozzle rows 40 and columns 41 similar to the array of wells 26. In the preferred form, the number of nozzle rows 40, each extending parallel to a longitudinal axis 42 of head assembly 21, is equivalent to the number of well rows 34. Accordingly, each nozzle 22 in a particular bank or row 40 of nozzles corresponds to and is aligned with a respective column 36 of wells 26. The nozzles in any one row 40 and column 41 are also equally spaced-apart by the same distance as the spacing between the well rows 34 and columns 36 which permit simultaneous alignment between one or more well rows 34 with selected nozzle rows 40 during a single cycle. That is, the array of wells can be aligned with the array of nozzles along a plurality of positions for simultaneous deposition.

This array technique for sequence defined oligonucleotide synthesis first evolved from the high density oligonucleotide array chip assembly for hybridization sequencing disclosed in U.S. patent application, Ser. No. 07/754,614, filed Sep. 4, 1991, now pending. Hence, this array technique, alone, is not claimed as a novel feature of the present invention. That assembly, however, is neither suitable nor appropriate for the large-scale production capabilities of the present invention as will be described henceforth.

To simplify organization and manufacture of polymer chains, a delivery assembly 43 (FIG. 7) of the synthesis apparatus, for controlling delivery of the liquid reagents through the array of nozzles, communicably couples all nozzles 22 in a particular bank or row 40 to a common independent liquid reagent reservoir 23, while each bank or row 40 of nozzles is coupled to a different liquid reagent applied in a particular polymer synthesis. For instance, the first row 40 of nozzles 22 may only dispense the activator tetrazole, while the second row of nozzles dispenses the amidite thymidine. In oligonucleotide synthesis, this order of liquid reagent distribution may continue down the line for the amidites adenosine, cytosine, and guanine, the auxiliary base AnyN, the solvent wash/reaction solvent acetonitrile, the Cap acetic anhydride, the Cap N-methylimidazole, iodine and the deblockers dichloracetic acid or trichloracetic acid; all of which are reagents used for the synthesis of defined sequence oligonucleotides. Incidently, only five rows of nozzles are shown for the ease of illustration.

Further, it will be understood that any nozzle contained in the array may be communicably coupled to any reagent reservoir.

The delivery assembly 43 of the present invention communicably couples each bank of nozzles to a common reagent reservoir 23 through independent dispensing tubes 44. Each tube includes a passageway 45 (FIG. 6) and has one end coupled to the respective nozzle and an opposite end terminating in the liquid reagent 24 contained in the reservoir. These tubes are press-fit into apertures 46 extending through mounting blocks 37 and a head plate 47 of head assembly 21. The flexible and semi-resilient nature of each tube 44, preferably TEFLON® which are more resistant to deterioration upon contact with the reagents, provides an adequate seal between the tubing exterior and the respective aperture.

A distal end of each tube 44, as shown in FIGS. 2 and 6, forms nozzle 22 which extends into, but not past, transversely positioned slots 50 which are formed in a bottom surface 51 of head plate 47. Accordingly, each independent nozzle 22 is recessed so as not to interfere with a top surface 52 of base sliding plate 33 during relative sliding movement therebetween. Further, the independent extension of each nozzle into slots 50 promotes removal or discarding of residual liquid reagent accumulated at the end of the nozzle after delivery of reagent therefrom.

There are two important concerns in liquid reagent delivery through nozzles 22: 1) how to eject a droplet cleanly so that a drop is not left hanging on the end of the nozzle; and 2) how to keep the contents of the reaction chamber from splashing when the stream of reagent is delivered into the well. Further, the ejection velocity of the reagent from the nozzle must be sufficient to induce mixing between the first and second delivered reagent in the reaction chamber. Very small droplets can be ejected cleanly at high ejection velocities, but do not have sufficient kinetic energy to overcome the surface tension of the liquid already in the well to cause mixing. In contrast, larger droplets also eject cleanly at high ejection velocities, but tend to splash the contents into adjacent wells. At lower ejection velocities, the reagents tend to leave the last drop hanging from the nozzle tip, which is also a function of the cross-sectional area of the tip. Moreover, the flow rate of liquids through small capillary tubing varies directly with the delivery pressure and inversely with the length of the tube and inversely with the diameter. All these variables must be taken into consideration when developing delivery pressure and nozzle configurations, as well as the materials of construction, so that the reagents can be expelled cleanly without leaving a residual drop of liquid reagent hanging from the nozzle tip. Hence, depending on the liquid reagent, it may be more beneficial to dispense it in a continuous stream, a series of pulses or in droplet form.

Each reagent reservoir 23, as shown in FIG. 7, includes a pressure tube 53 coupled to a compressor device (not shown) which pressurizes reservoir air space 54 to drive the stored liquid reagent from the reservoir and through respective dispensing tubes 44. Delivery of reagents through dispensing tubes 44 is controlled by an array of independent valve assemblies 55 each mounted in-line therewith. These valve assemblies are preferably provided by solenoid driven micro shutoff valves, each capable of opening and closing in less than 5 milliseconds to deliver accurate volumes of liquid reagent.

To assure a constant delivery pressure across each dispensing tube 44, and hence, a constant delivery rate of liquid reagent through any nozzle in a bank or row 40 of nozzles 22, each dispensing tube will independently terminate in the liquid reagent contained in the reagent reservoir. Thus, independent of the number of nozzles set to deliver, this configuration will not suffer uneven rate delivery caused by varying line pressure.

In accordance with the present invention, base assembly 25 and head assembly 21 cooperate with transport mechanism 27 for relative movement between the base assembly and the head assembly to align the array of wells with the array of nozzles at a plurality of positions. Preferably, the transport mechanism moves the base assembly along (phantom lines in FIG. 3) its longitudinal axis 35 such that the wells of each row 34 remain aligned with the nozzle columns 41. Base assembly 25 is, thus, slidably supported by frame assembly 57 (FIGS. 3 and 4) for reciprocating movement in the direction of arrows 60. Sliding plate 33, carrying microtiter plate 32, is slidably received in a track mechanism 61 of frame assembly 57 for aligned movement. Hence, by controlling the delivery of reagent through selected nozzles (via valve assemblies 55), and through manipulation of the transport mechanism, a plurality of homogenous populations of sequence defined polymers can be simultaneously synthesized in selected wells in a rapid and reproducible manner.

Transport mechanism 27 includes a stepped motor assembly 62, schematically represented in FIG. 3, which is operably coupled to sliding plate 33. Hence, base assembly 25 cooperates with track mechanism 61 and the stepped motor for linear incremental movement to align the array of wells with the array of nozzles at a plurality of positions. It will be understood, however, that the transport mechanism can be provided by any motor/track configuration which moves the base assembly relative the head assembly.

Before polymer synthesis begins or after the synthesis process has ended, the array of wells may be positioned outside of common chamber 31 and exposed to the open environment for access by moving the wells 26 (via movement of base assembly 25) to the extreme right or left of sliding seal 30. Hence, the well array may be cleaned or loaded with solid support material, to be discussed. Further, the wells and nozzles, once inside the common chamber, may be accessed through a hinge assembly 63, as shown in FIG. 4, which pivotally mounts head assembly 21 to frame assembly 57.

Referring now to FIGS. 1, 3 and 5, the sliding seal of the present invention will be described. In oligonucleotide synthesis by phosphoramidite coupling, there are two major chemical engineering requirements because the coupling reactions are rapid and irreversible: water and oxygen are preferably both be excluded from the common reaction chamber during synthesis. Phosphoramidites are sensitive to hydrolysis by tracing of water, and to oxidation by contact with air. Sliding seal 30, therefore, is disposed between the bottom surface 51 of head assembly 21 and the top surface 52 of base assembly 25 to environmentally contain both the reaction wells and the nozzles in a common chamber 31. Further, as will be described in greater detail below, by streaming an inert gas through common chamber 31 to sweep the air and water traces from the chamber, hydrolysis and oxidation can be minimized, if not eliminated.

Sliding seal 30 must be formed to maintain environmental containment while permitting the base assembly to slide relative the head assembly. In the preferred form, sliding seal 30 is provided by an elastic, rectangular-shaped, hydrofoil or balloon seal gasket having an upper end mounted to head bottom surface 51, and an opposite or lower end 64 in sliding contact with base top surface 52. This special gasket, preferably composed of rubber or the like, increases seal integrity between gasket lower end 64 and base top surface 52 as the pressure in common chamber increases. FIG. 5 illustrates that gasket lower end 64 peripherally tapers inwardly toward an interior of common chamber 31. Upon increase in chamber pressure, the walls of gasket seal 30 expand outwardly whereby the surface area contact between the gasket lower end and the base top surface increases for better sealing engagement therebetween.

To facilitate sliding contact, while maintaining environmental containment, gasket seal 30 includes a stick-free coating or layer 65 (FIG. 5), preferably TEFLON®, between the gasket lower end and the base top surface. This layer further serves the purpose of protecting the sealing gasket from surface absorption of residual liquid reagents which tend to deteriorate the gasket upon contact, due in part to the elastic nature thereof. As shown in FIG. 5, top surface 52 of the base assembly may also include a coating or layer 66 of TEFLON® to promote sliding contact and for protection of the top surface from residual reagent.

It will be understood that the seal between gasket lower end 64 and base top surface 52 need not be hermetic. The primary function of the seal gasket is to exclude oxygen from the reaction chamber. Thus, it is important to normally maintain a minimum positive pressure inside common chamber 31 at all times during synthesis which is slightly greater than atmospheric pressure so that the flow of gas, should a leak occur, would be outward. This minimum positive pressure differential is generally about 1/100 psi to about 1/10 psi.

As previously indicated and as viewed in FIGS. 3, 5 and 6, it is desirable to flush the air and water traces from the reaction head space of the chamber with an inert gas, preferably argon, to minimize hydrolysis and oxidation of the amidites during synthesis. It is further desirable to continuously stream the inert gas through the head space to protect sensitive amidites from the capping and deblocker reagents, such as aqueous iodine vapor or trichloroacetic acid, which will react with the amidites. This is accomplished by introducing a flow of inert gas (represented by arrows 67) through common chamber 31 from a gas inlet 70, positioned upstream from the array of nozzles 22, which exits the chamber through a gas outlet 71 positioned downstream from the nozzles. Gas inlet 70 is coupled to a gas source (not shown) through inlet tube 72 (FIG. 1) which further provides the positive pressure inside common chamber 31 necessary to exclude the oxygen from the environment. Since the head space of the common chamber is relatively small (exaggerated in the FIGURES for illustration), a sufficient flow of gas past the nozzles can be fashioned to sweep or flush the chamber without expending large volumes of gas.

The gas inlet is preferably provided by an elongated inlet slot 70 (FIG. 2) extending into head plate 47 and aligned transverse to the longitudinal axis 42 of head plate 47. This shape and orientation induces a substantially laminar flow of inert gas from upstream inlet 70 to downstream outlet 71 which minimizes cross flow of gas across the nozzles and sweeps the dead zones of stagnant reagent vapors from the chamber. It will be noted that the gas inlet may also be provided by a series of apertures extending transversely across head plate 47, and that gas outlet 71 may further be provided by an elongated slot or series of apertures.

Because of the gas flow through the chamber, the acid and moisture sensitive phophoramides are positioned upstream from the deblocker and capping reagents, forming a diffusion gas barrier, which maximizes the sweeping effect. Accordingly, in FIG. 3, the phosphoramides would be dispensed from nozzles 22 closer to gas inlet 70, while the cappers, washers and deblockers would be dispensed from the nozzles situated closer to gas outlet 71, downstream from the phosphoramide dispensing nozzles.

In another aspect of the present invention, as best viewed in FIGS. 5 and 6, polymer synthesis apparatus 20 is provided with reaction wells 26 having at least one orifice, generally designated 74, extending into the well. At least one solid support 75 is disposed in the well for growing and immobilizing a polymer chain thereon. Reagent solution 76 in well 26 is in contact with solid support 75 and at least one polymer unit of the polymer chain affixed to the solid support. Orifice 74 has an entrance 77 into well 26 from the common chamber side and an exit 80 out of the well into a lower catch basin 81 below. Importantly, the orifice is of a size and dimension to form a capillary liquid seal with reagent solution 76 contained therein to retain the reagent solution in the well enabling polymer chain growth therein. To further retain solution 76 in wells 26, a pressure differential between a common chamber gas pressure exerted on the reagent solution in reaction wells 26 and a second gas pressure exerted on orifice exits 80 (illustrated by arrows 79 in FIG. 6) must be less than a predetermined amount. Finally, a pressure regulating device 82 is provided for controlling the pressure differential such that upon the pressure differential exceeding the predetermined amount, the reagent solution 76 is expelled from well 26 through orifice 74 (FIG. 5).

Briefly, after proper alignment between selected wells 26' with selected nozzles 22' (FIG. 6), using the array technique and novel apparatus above-mentioned, the liquid reagents can be deposited into selected wells 26'. The deposited reagent solutions collects across the correctly dimensioned orifice 74, in combination with a relatively small pressure differential (not greater than the predetermined amount), to form a meniscus across orifice 74 and creating a capillary liquid seal to retain the solution in the well without draining through the orifice. This seal effectively separates the common reaction chamber from the environment of lower catch basin 81 below. After a sufficient amount of time has passed to complete the synthesis reaction (generally about one minute), the reagent solution is purged from well 26 through orifice 74 and into lower catch basin 81 by increasing the gas pressure differential above the predetermined amount which overcomes the capillary forces in the orifice (FIG. 5). Subsequently, the purged reagent solutions may be drawn out of the catch basin through a drain outlet 83. This process is repeated for each synthesis cycle (i.e., deblocking, washing, coupling, capping and oxidizing steps) until the desired defined synthesis polymer is fabricated.

A retaining device, generally designated 84, is included positioned in the bottom of well 26 between orifice 74 and the solid support 75 which is formed and dimensioned to substantially prevent passage of the solid support through the orifice. Retaining device 84 is preferably provided by a polyethylene or glass fiber frit which acts as a filter membrane permitting the reagent solution to flow therethrough while retaining the solid support and polymer chain grown thereon in the well. Hence, the porosity of the frit is also a factor in the formation of the capillary liquid seal and in the determination of the pressure differential necessary to purge the reaction well.

To regulate and control pressure differential between common chamber 31 and lower catch basin 81, as mentioned, pressure regulating device 82 is provided operably coupled therebetween. In the preferred embodiment, pressure regulating device 82 is integrated with the gas flow assembly employed to flush the head space in common chamber 31 of reagent toxins. Upon the inert gas freely sweeping the chamber from gas inlet 70 to gas outlet 71, the minimum pressure differential is generally retained between about 1/100 psi to about 1/10 psi. This pressure differential which is sufficiently positive to prevent seepage of environmental air into the common chamber, while being insufficient to overcome the capillary forces of the capillary liquid seal in each well. By preventing or restricting the outflow of inert gas through gas outlet 71, the pressure inside chamber 31 can be increased, thereby increasing the pressure differential to purge the wells (FIG. 5) if the catch basin pressure is not increased at the same or greater rate.

The pressure regulating device 82, hence, includes a chamber valve 85 (FIG. 1) coupled to gas outlet 71 for controlling the outflow of inert gas sweeping common chamber 31. Accordingly, by sufficiently closing or restriction flow through chamber valve 85, the pressure differential can be raised above the predetermined amount so that the wells can be purged of reagent solution simultaneously. Similarly, by sufficiently opening chamber valve 85, the pressure differential may be lowered below the predetermined amount when it is desired to retain the deposited liquid solution in the selected wells.

The liquid reaction solution will not leak out of or be purged from well orifice 74 until there is a sufficient head of liquid in the well or a sufficient gas pressure differential between the common chamber and the lower catch basin to overcome the capillary forces in the orifice. The rate of gravity-driven and pressure-driven leakage from the orifice is primarily governed by the viscosity of the solvent, the porosity of the frit, the size of the orifice, and the gas pressure differential. For instance, a 10µ UHMW polyethylene frit and a 0.015 in$^2$ orifice will support at least 0.79 in. liquid head of acetonitrile (having a viscosity of about 0.345 centipose ($7.2 \times 10^{-5}$ (lbf·s)/ft$^2$ at an operating temperature of about 68° F.)) before beginning to overcome the capillary forces in the orifice. On the other hand, by increasing the pressure differential above the predetermined amount (generally about 1 psi) to about 5 psi, purging of the well will occur rapidly. In practice, it is necessary to maintain a pressure differential between about 2.5 psi to about 5 psi to sufficiently purge the reaction wells simultaneously of reagent solution. As the individual wells begin to empty, the flow rate of inert gas through the empty wells of the microtiter plate substantially increases which decreases the pressure in common chamber 31. Accordingly, this decrease in interior pressure further decreases the purging or draining rate of the reagent solution through the orifices, an effect magnified by retaining filter membrane 84.

It will be appreciated that the pressure differential may also be created by forming a vacuum in lower catch basin 81 to purge the reaction wells. FIG. 1 illustrates that an access opening 86 into lower catch basin 81 may be sealed by a cover 87, and drain outlet 83 may be coupled to a vacuum pump which creates a vacuum in the basin. The pressure differential may also be created from a combination of positive pressure in common chamber 31 and a vacuum in catch basin 81. Further, since the reagent solution is allowed to collect in the reaction well for reaction thereof rather than continuously streaming through the chamber, as is employed by some other prior art assemblies, reagent consumption is substantially minimized thereby saving costs. Labor costs are also reduced by minimizing each cycle time.

To coordinate all the simultaneous functions, a control mechanism 90 (FIG. 7) is operably coupled between transport mechanism 27, valve assemblies 55 and pressure regulating device 82. A sequence file can be input which contains an ordered list of the well position, scale, final deblocking instruction and the ATGC and N (odd Base) sequence for each oligonucleotide. This file cooperates with a command file used to indicate the actual number and order of Deblock/Wash/Couple/Cap/Oxidize steps and the length of time for Wait and pressure and/or vacuum Drain steps which define the complete coupling cycle.

Oligonucleotides are typically synthesized on solid supports of controlled pored glass (CPG) having the first nucleotide previously linked to the CPG through the 3'-succinate linkage. Hence, upon preparation for polymer synthesis, each well is individually loaded with the correct CPG derivative. While one could begin a full plate of synthesis using only one CPG derivative, for example T (i.e., dT-Icaa-CPG), it is more desirable to perform array synthesis where any base can be in the first position. However, individually weighing and transferring 0.5 mg quantities of the appropriate dry CPG derivative to each well can be tedious and time consuming.

In accordance with the present invention, a balanced density slurry technique is employed to deposit the correct amount of CPG into a reaction well. By suspending the CPG in a suspension solution, a desired amount of CPG can be accurately deposited in a well by pipetting, either automatically or manually, a corresponding volume of suspension solution therein. For example, a non-settling 10%→1% weight/volume suspension of CPG can be prepared in a 2.5:1 volume/volume dibromomethane-dichloromethane solution. Subsequently, the CPG can be washed and purged of suspension solution before synthesis using the technique mentioned above.

In another aspect of the present invention, a method of synthesis of a polymer chain is provided comprising the steps of: A) aligning reaction well 26 and a selected one nozzle 22 of synthesis apparatus 20 through transport mechanism 27 coupled to at least one of head assembly 21 and base assembly 25 to produce relative movement therebetween; and B) depositing a liquid reagent 24 into well 26 from reagent reservoir 23 through the one nozzle to enable synthesis of a polymer chain. Finally, C) sweeping toxic fumes, emitted by the reagents, from common chamber 31 through passage of a gas from a pressurized gas source, coupled to an inlet 70 into common chamber 31 and positioned upstream from the nozzles, and out of the chamber through an outlet 71 out from the common chamber and positioned downstream from the nozzles.

Another method of polymer synthesis is provided for building a polymer chain by sequentially adding polymer units to at least one solid support for growing and immobilizing a polymer chain thereon in a liquid reagent. The method comprises the steps of A) depositing liquid reagent 24 in reaction well 26, having a properly sized orifice 74, in contact with at least one solid support 75 and at least one polymer unit of the polymer chain affixed to solid support 75, and forming a capillary liquid seal to retain the reagent solution in well 26 to enable polymer chain growth on solid support 75. The next step includes B) applying a first gas pressure to reaction chamber 31 such that a pressure differential between the first gas pressure and a second gas pressure exerted on an exit 80 of orifice 74 exceeds a predetermined amount necessary to overcome the capillary liquid seal and expel the reagent solution from well 26 through orifice 74.

By repeating the steps of the two above-mentioned methods, one continuous chain of polymer units can be formed.

The following example serves to more fully describe the manner of using the above-described invention, as well as to set forth the best mode contemplated for carrying out various aspects of the invention. It is to be understood that this example in no way serves to limit the true scope of the invention, but rather are presented for illustrative purposes. It is to be understood that any method of oligonucleotide synthesis may be utilized in the present invention.

EXAMPLE 1

Synthesis of an Array of 15 Oligonucleotides

The general synthesis procedure follows published procedures for the phosphoramidite and hydrogen phosphonate methods of oligonucleotide synthesis; for example, the methods outlined in Oligonucleotides and Analogues: A Practical Approach, F. Eckstein, Ed. IRL Press, Oxford University; Oligonucleotide Synthesis: A Practical Approach, Gait, Ed., IRL Press, Washington D.C.; and U.S. Pat. Nos. 4,458,066, 4,500,707 and 5,047,524, all hereby incorporated by reference. It is to be understood that other methods of oligonucleotide synthesis may be used in the present invention.

In general, the basic steps of the synthesis reaction are as follows, with appropriate acetonitrile washing steps:

a) the first nucleoside, which has been protected at the 5' position, is derivatized to a solid support, usually controlled pore glass (CPG), or is obtained prederivatized;

b) the sugar group of the first nucleoside is deprotected or detritlyated, using tricholoraceticmethylene chloride acid, which results in a colored product which may be monitored for reaction progress;

c) the second nucleotide, which has the phosphorus, sugar and base groups protected, is added to the growing chain, usually in the presence of a tetrazole catalyst;

d) unreacted first nucleoside is capped to avoid perpetuating errors, using acetic anhydride and N-methylimidazole;

e) the phosphite triester is oxidized to form the more stable phosphate triester, usually using iodine reagents;

f) the process is repeated as needed depending on the desired length of the oligonucleotide; and g) cleavage from the solid support is done, usually using aqueous ammonia at elevated temperatures over a period of hours.

Accordingly, a sequence file was generated which indicated the 3'-5' sequence and well number for each oligonucleotide to be synthesized, the scale of the reaction for each nucleotide, and whether a final detritylation was to be performed on the product at the end of the reaction. The software was designed to support simultaneous independent synthesis of oligonucleotides of different lengths and scale. The sequence of the 15 different oligonucleotides is shown in Table 1 below.

TABLE 1

| Number | Sequence | | | | | | |
|---|---|---|---|---|---|---|---|
| 1 | AAG | TCT | TGG | ACT | TAG | AAG | CC |
| 2 | GGG | TCA | CTT | CTT | TGT | TTT | CG |
| 3 | CCT | TTA | CTT | TTC | GGT | CAA | GG |
| 4 | TGA | CTG | GTA | GGT | CCA | CTG | CA |
| 5 | ACC | TCA | CTT | CGG | TAA | CTT | AAA |
| 6 | CCA | AAT | TTT | GAG | GTA | ACC | ACT T |
| 7 | GTG | CTA | TCC | GGG | ACA | CCA | |
| 8 | GGA | AGA | TCC | ACG | AGT | CGT | TT |
| 9 | CGT | CCA | CCT | CTT | CTT | TGA | AGA |
| 10 | TGG | TAG | TAA | TCC | TAC | CGT | CT |
| 11 | GCG | AAG | GTC | TAC | TCT | CGT | C |
| 12 | GTT | CAG | AGT | AAG | GAG | TCG | TGG |
| 13 | GTG | GAA | CCA | TAG | ACA | ACC | ACA TAT |
| 14 | TTG | TTC | ATC | TTT | GTG | TAG | GGT AC |
| 15 | AGA | AAA | GTC | ACG | GTC | ACA | CT |

A command file was generated which contained the sequence of reaction steps performed during a coupling cycle. The basic commands were WASH (volume), DEBLOCK (volume), COUPLE, CAP, OXIDIZE, WAIT (seconds) and DRAIN (pressure/vacuum seconds), as shown in Table 2 below:

TABLE 2

| Step Number | Step | Volume (λ) | Time (sec) |
|---|---|---|---|
| 1 | Deblock | 125 | |
| 2 | Wait | | 5 |
| 3 | Drain | | 15 |
| 4 | Wash | 200 | |
| 5 | Drain | | 15 |
| 6 | Wash | 300 | |
| 7 | Drain | | 20 |
| 8 | Wash | 200 | |
| 9 | Drain | | 20 |
| 10 | Couple | | |
| 11 | Couple | | |
| 12 | Wait | | 150 |
| 13 | Drain | | 10 |
| 14 | Wash | 200 | |
| 15 | Drain | | 15 |
| 16 | Cap | | |
| 17 | Wait | | 40 |
| 18 | Drain | | 10 |
| 19 | Wash | 200 | |
| 20 | Drain | | 15 |
| 21 | Oxidize | | 40 |

TABLE 2-continued

| Step Number | Step | Volume (λ) | Time (sec) |
|---|---|---|---|
| 22 | Wait | | 10 |
| 23 | Drain | 300 | |
| 24 | Wash | | 20 |
| 25 | Drain | 200 | |
| 26 | Wash | | 20 |
| 27 | Drain | | |

A configuration file was generated which contained the operating characteristics of the machine, the liquid flow rates, the concentration and molar equivalents used for each of the reagents, as shown in Table 3 below.

TABLE 3

| reagent | concentration | flow rate | molar excess |
|---|---|---|---|
| acetonitrile | | 220λ/sec | |
| trichloroacetic-methylene chloride acid | | 125λ/sec | |
| tetrazole | 0.45M | 210λ/sec | 250 |
| acetic anhydride | | 210λ/sec | 500 |
| N-methylimidazole | | 210λ/sec | 500 |
| iodine | | 210λsec | 150 |
| phosphoramidite | 0.1M | 210λsec | |

96 well plates were used which have a conical lower section which has been recessed to receive a pressed-fit 0.196 inch filter disk. Below the filter was the flow restriction and capillary liquid seal orifice, 0.020 inch diameter × 0.350 inch length. The outside diameter of the capillary seal at the exit tip was 0.035 inch. When fitted with Whatman GF/A filters, the gas flow rate through a completely dry plate at an upper chamber pressure of 1 psi was 10 liters per minute. At 0.02 psi upper chamber pressure, the capillary seal at the bottom of the synthesis well supported an acetonitrile liquid head of approximately 1 cm above the filter before slow leakage commenced. The plates were fabricated of molded polypropylene.

To each well was added the correct amount of CPG with derivatized first base, either A, T, C, or G. For example, 0.5 mg CPG was used in a 20 nanomole scale reaction. The CPG beads were added as a slurry in dibromomethane-chloroform pipetted into each well. This step was performed in ordinary lab atmosphere prior to loading the plate into the machine. After loading the plate into the machine, a WASH acetonitrile cycle was done to rinse the slurry, and to verify that all wells were draining properly.

The nozzle valve reservoirs were flushed with argon and then filled with fresh reagents from the supply bottles by pressurized transfer to avoid air and water contamination. The valve reservoirs were then pressurized to the configuration pressure (4 psi). The nozzle tubing was then primed by dispensing a small amount of liquid with the sliding plate in the purge position for each reagent.

During reagent addition and reaction wait periods, the laminar gas sweep flow across the reaction chamber was regulated to 0.4 liter per minutes with an internal pressure of approximately 0.02 psi. During spent reagent removal and washing cycles, the chamber pressure was increased to a maximum of 5 psi. At 2.5 psi, the synthesis wells drained at a rate of approximately 150 λ/sec.

The machine was then switched into AUTOmatic mode in order to commence actual synthesis. The machine paused during the first, second and last cycles in order to allow collection of the DEBLOCK trityl products for colorimetric analysis. This was accomplished by sliding a second 96-well microtiter plate into the lower vacuum/drain chamber, immediately beneath the capillary exit tips of the synthesis plate. The optical density of detritylation solution at 490 nanometers was read using a plate reader. The value for the first cycle confirmed the amount of CPG loaded into a well, and comparison of the second cycle with the last cycle permitted calculation of the synthesis coupling efficiency. The final cycle value also indicated the amount of oligonucleotide which will be obtained after sidechain deprotection by ammonia cleavage.

After the machine completed the synthesis in all the wells, the synthesis plate was removed from the machine. The synthesis plate was stacked on top of a second 96 well deprotection plate (Beckman deep-well titer plate 267001). The oligonucleotides were cleaved from the support by pipetting 200 microliters of concentrated $NH_4OH$ into each well followed by incubation at 25° C. for 15 minutes. The ammonium cleavage solutions were eluted through the filter and capillary exit into the wells of the deprotection plate by pressure, vacuum or preferably brief centrifugation of the stack. This cleavage step was repeated twice with fresh aliquots of ammonia.

If the phosphoramidites used for synthesis had benzoyl and isobutyryl protecting groups, the final deprotection was completed by heating the crude ammonia cleavage product. The wells of the deprotection titer plate were sealed with a dimpled silicon rubber cap (Beckman 267002), and the caps held in place using a spring-loaded plate press. The sealed apparatus was heated in an air oven or water bath at 55° C. for 8–15 hours, and then cooled in an ice bath. The deprotection plate was removed from the press and centrifuged briefly prior to removing the cap.

The ammonia solution was then evaporated to dryness using a Savant 210 Speed Vac equipped with a microplate rotor. The oligonucleotide pellets thus obtained were generally sufficiently pure for use directly in most sequencing primer and PCR applications. The amount of oligonucleotide predicted by the last trityl assay was verified by optical density at 260 nanometers, and the homogeneity of the product assayed by HPLC or capillary gel electrophoresis. Capillary electrophoresis analysis was performed on an Applied Biosystems 270A instrument according to the manufacturer's protocols for oligonucleotides 14 and 15 from the above run are shown in FIGS. 8A and 8B, respectively. Typical yields for a 20 nanomolar scale synthesis of a 20-mer were 2.5 OD (85 micrograms).

What is claimed is:

1. A polymer synthesis apparatus for building a polymer chain by sequentially adding polymer units to a solid support in a liquid reagent comprising:

a base assembly including a reaction well, and having at least one orifice extending into said well;

at least one solid support disposed in said well for growing and immobilizing a polymer chain thereon;

reagent solution in said well in contact with said solid support and at least one polymer unit of said polymer chain affixed to said solid support;

retaining means positioned in said well, and formed and dimensioned to substantially prevent passage of said solid support through said orifice;

said orifice having an entrance into said well and an exit, and being of a size and dimension to form a capillary liquid seal to retain said reagent solution in said well to enable polymer chain growth therein when a pressure differential between a first gas pressure exerted on said reaction well and a second gas pressure exerted on said orifice exit is less than a predetermined amount; and a pressure regulating device for controlling said pressure differential such that upon said pressure differential exceeding said predetermined amount, said reagent solution being expelled from said well through said orifice.

2. The polymer synthesis apparatus as defined in claim 1 wherein, said retaining means comprises a filter member disposed in said well between said one orifice and said support structure.

3. The polymer synthesis apparatus as defined in claim 2 wherein, said filter member is composed of a glass fiber frit.

4. The polymer synthesis apparatus as defined in claim 2 wherein, said filter member and said orifice cooperate in a manner forming said capillary liquid seal.

5. The polymer synthesis apparatus as defined in claim 1 further including:

a top chamber mechanism cooperating with a top surface of said base assembly to form a top chamber enclosing said reaction well therein, said regulating device communicating with said top chamber to regulate said pressure differential.

6. The polymer synthesis apparatus as defined in claim 1 wherein, said solid support is provided by controlled pore glass (CPG).

7. The polymer synthesis apparatus as defined in claim 1 wherein, said polymer chain is an oligonucleotide.

8. The polymer synthesis apparatus as defined in claim 1 further including:

a bottom chamber mechanism cooperating with a bottom surface of said base assembly to form a bottom chamber enclosing said orifice therein, said regulating device communicating with said bottom chamber to regulate said pressure differential.

9. A polymer synthesis apparatus for building a polymer chain by sequentially adding polymer units in a liquid reagent, said apparatus comprising:

a frame assembly;

a base assembly movably mounted to said frame assembly and including an array of reaction wells aligned in a plurality of spaced-apart well rows and columns, each well having at least one respective orifice extending into said well;

a head assembly mounted to said frame assembly and having an array of nozzles aligned in a plurality of nozzle rows and columns spaced-apart by a distance substantially similar to the spacing between said well rows and columns for alignment therebetween, each nozzle being coupled to a reservoir of liquid reagent for controlled delivery therethrough;

a transport mechanism coupled to said base assembly for moving support, relative said head assembly, along a path substantially parallel to said nozzle columns to position at least one row of reaction wells in depository alignment with a selected row of nozzles for simultaneous deposition of a liquid reagent into selected reaction wells for synthesis of polymer chains;

a sliding seal positioned between said head assembly and said base assembly, and enclosing all said reaction wells and all said nozzles therein to form a common chamber;

each said well orifice being of a size and dimension to form a capillary liquid seal to retain said deposited liquid reagent in said selected wells to enable polymer chain growth therein when a pressure differential between a first gas pressure in said chamber and a second gas pressure exerted each orifice exit is less than a predetermined amount; and a pressure regulating device for controlling said pressure differential such that upon said pressure differential exceeding said predetermined amount, said liquid reagent being expelled from respective wells through respective orifices.

10. The polymer synthesis apparatus as defined in claim 9 wherein, said sliding seal is provided by a balloon seal having one end affixed to a bottom surface of said head assembly, and an opposite end in sliding contact with a top surface of said base assembly.

11. The polymer synthesis apparatus as defined in claim 10 wherein, said transport mechanism includes a stepped motor operably coupled to said base assembly for linear incremental movement of said reactions wells along said path.

12. The polymer synthesis apparatus as defined in claim 11 wherein, respective nozzles of each nozzle row are coupled to one reagent reservoir of said plurality of independent reagent reservoirs.

13. The polymer synthesis apparatus as defined in claim 12 wherein, each nozzle communicates with said respective reagent reservoir through a tube forming a passageway and having one end coupled to said nozzle and an opposite end terminating in said reagent reservoir, and each tube includes a valve assembly in-line with said respective passageway to control passage of the reagent solution therethrough.

14. The polymer synthesis apparatus as defined in claim 13 wherein, said pressure regulating device includes an inlet into said common chamber positioned upstream from said array of nozzles, an outlet out of said common chamber positioned downstream from said array of nozzles, and a pressurized gas source coupled to said inlet for continuously streaming a gas from said gas source through said common chamber from said chamber upstream to said chamber downstream and out said outlet to sweep said chamber of toxic fumes emitted by said reagents.

15. The polymer synthesis apparatus as defined in claim 14 wherein, said regulating device further includes a chamber valve coupled to said outlet controlling outflow of said gas from said chamber for one of raising said pressure differential above said predetermined amount and lowering said pressure differential below said predetermined amount.

16. A polymer synthesis apparatus for building a polymer chain by sequentially adding polymer units in a reagent solution, said apparatus comprising:

a head assembly having a plurality of nozzles mounted thereto in generally spaced-apart relation, each nozzle being coupled to a reservoir of liquid reagent for controlled delivery therethrough;

a base assembly having at least one reaction well, and at least one orifice extending into said well;

a transport mechanism coupled to at least one of said head assembly and said base assembly to produce relative movement therebetween to position said reaction well and a selected one nozzle in alignment for deposition of a liquid reagent into said reaction well for synthesis of a polymer chain;

said orifice having an entrance into said well and an exit, and being of a size and dimension to form a capillary liquid seal to retain said deposited liquid reagent in said well to enable polymer chain growth therein when a pressure differential between a first gas pressure in said chamber and a second gas pressure exerted on said orifice exit is less than a predetermined amount;

a pressure regulating device for controlling said pressure differential such that upon said pressure differential exceeding said predetermined amount, said reagent solution being expelled from said well through said orifice; and a sliding seal positioned between said head assembly and said base assembly forms a common chamber enclosing both said reaction well and said nozzles therein.

17. The polymer synthesis apparatus as defined in claim 16 further including:

at least one solid support disposed in said well for growing and immobilizing said polymer chain thereon;

said liquid reagent deposited in said well in contact with said solid support and at least one polymer unit of said polymer chain affixed to said solid support; and retaining means positioned in said well, and formed and dimensioned to substantially prevent passage of solid support through said orifice.

18. The polymer synthesis apparatus as defined in claim 16 wherein, said pressure regulating device includes an inlet into said common chamber positioned upstream from said nozzles, an outlet out of said common chamber positioned downstream from said nozzles, and a pressurized gas source coupled to said inlet for continuously streaming a gas from said gas source through said common chamber from said chamber upstream to said chamber downstream and out said outlet to sweep said chamber of toxic fumes emitted by said reagents.

19. The polymer synthesis apparatus as defined in claim 18 wherein, said regulating device further includes a chamber valve coupled to said outlet controlling outflow of said gas from said chamber for one of raising said pressure differential above said predetermined amount and lowering said pressure differential below said predetermined amount.

20. The polymer synthesis apparatus as defined in claim 18 wherein, said inlet and said outlet are defined by said head assembly.

21. The polymer synthesis apparatus as defined in claim 16 wherein, said base assembly includes a top surface defining said well, and a opposite facing bottom surface, said orifice extending from said bottom surface to said top surface and into said well, and said synthesis apparatus further including:

a bottom chamber mechanism cooperating with said base bottom surface to form a bottom chamber enclosing said orifice therein, said regulating device communicating with said bottom chamber to form a vacuum for regulation of said pressure differential.

22. A polymer synthesis apparatus for building a polymer chain by sequentially adding polymer units in a reagent solution, said apparatus comprising:

a base assembly defining a plurality of wells aligned in an array spaced-apart rows and columns;

a head assembly having a plurality of nozzles aligned in an array having nozzle rows and columns spaced-apart by a distance substantially similar to the spacing between said spaced-apart well rows and columns for simultaneous alignment therebetween, each nozzle being coupled to one reservoir of a plurality of independent reagent reservoirs each including a different liquid reagent for selective, sequential and controlled delivery in said well in a predetermined manner through a respective nozzle;

a transport mechanism coupled to at least one of said head assembly and said base assembly to produce relative movement therebetween to align any one selected nozzle with any one well for deposition of a liquid reagent into said one reaction well for synthesis of a polymer chain;

each reaction well including at least one respective orifice extending into a respective well, each orifice having an entrance into said well and an exit, and being of a size and dimension to form a capillary liquid seal to retain the deposited liquid reagent in selected wells to enable polymer chain growth therein when a pressure differential between a first gas pressure in said chamber and a second gas pressure exerted each orifice exit is less than a predetermined amount; and a sliding seal positioned between said head assembly and said base assembly to form a common chamber enclosing both said reaction well and said nozzles therein.

23. The polymer synthesis apparatus as defined in claim 22 further including:

a pressure regulating device for controlling said pressure differential such that upon said pressure differential exceeding said predetermined amount, said reagent solution being expelled from said well through said orifice.

24. The polymer synthesis apparatus as defined in claim 23 wherein, said pressure regulating device includes an inlet into said common chamber positioned upstream from said array of nozzles, an outlet out of said common chamber positioned downstream from said array of nozzles, and a pressurized gas source coupled to said inlet for continuously streaming a gas from said gas source through said common chamber from said chamber upstream to said chamber downstream and out said outlet to sweep said chamber of toxic fumes emitted by said reagents.

25. The polymer synthesis apparatus as defined in claim 24 wherein, said regulating device further includes a chamber valve coupled to said outlet controlling outflow of said gas from said chamber for one of raising said pressure differential above said predetermined amount and lowering said pressure differential below said predetermined amount.

26. The polymer synthesis apparatus as defined in claim 25 wherein, said inlet and said outlet are defined by said head assembly.

27. The polymer synthesis apparatus as defined in claim 26 wherein, said inlet is provided by an inlet slot extending substantially transversely across said common chamber such that said continuous stream is substantially laminar during passage by said array of nozzles.

28. The polymer synthesis apparatus as defined in claim 27 wherein, said outlet is provided by an outlet slot extending substantially transversely across said common chamber.

* * * * *